(12) United States Patent
Villanova et al.

(10) Patent No.: US 8,507,698 B2
(45) Date of Patent: Aug. 13, 2013

(54) ARTEMISININ DERIVATIVES FOR THE TREATMENT OF MELANOMA

(75) Inventors: Luigi Villanova, Zollino (IT); Felicia Cisale, legal representative, Zollino (IT); Azzurra Villanova, Zollino (IT); Luciano Villanova, Zollino (IT)

(73) Assignee: Lachifarma S.R.L. Laboratorio Chimico Farmaceutico Salentino, Zollino (IT)

( * ) Notice: Subject to any disclaimer, the term of this patent is extended or adjusted under 35 U.S.C. 154(b) by 497 days.

(21) Appl. No.: 12/679,916

(22) PCT Filed: Sep. 25, 2008

(86) PCT No.: PCT/EP2008/008173
§ 371 (c)(1),
(2), (4) Date: Apr. 30, 2010

(87) PCT Pub. No.: WO2009/043538
PCT Pub. Date: Apr. 9, 2009

(65) Prior Publication Data
US 2010/0216869 A1    Aug. 26, 2010

(30) Foreign Application Priority Data
Oct. 4, 2007  (IT) ............................. MI2007A1915

(51) Int. Cl.
*C07D 309/00* (2006.01)
*A61K 31/335* (2006.01)

(52) U.S. Cl.
USPC ........................................ 549/358; 514/450

(58) Field of Classification Search
USPC ........................................ 549/358; 514/450
See application file for complete search history.

(56) References Cited

U.S. PATENT DOCUMENTS
6,307,068 B1    10/2001  Li et al.

FOREIGN PATENT DOCUMENTS
EP          0 535 719 A2    4/1993
WO          99/65914 A1    12/1999

OTHER PUBLICATIONS

International Search Report, dated Feb. 3, 2009, from corresponding PCT application.
Jin-Ming Wu et al., "Synthesis and cytotoxicity of artemisinin derivatives containing cyanoarylmethyl group", European Journal of Medicinal Chemistry, Jan. 1, 2001, pp. 469-479, vol. 36, XP-002236365.
Yi-Xin Chen et al., "Studies on Analogues of Qinghaosu (Arteannuin, Artemisinine). III. The Synthesis of Diacidesters and Mono Esters of Digydroqinghaosu", Yao Hsueh Hsueh Pao—Acta Pharmaceutica Sinica, Jan. 1, 1985, pp. 105-111, vol. 20, No. 2, XP-002119787.

*Primary Examiner* — Andrew D Kosar
*Assistant Examiner* — Raymond Covington
(74) *Attorney, Agent, or Firm* — Young & Thompson

(57) ABSTRACT

The invention relates to Artemisinin derivatives of general formula (I)

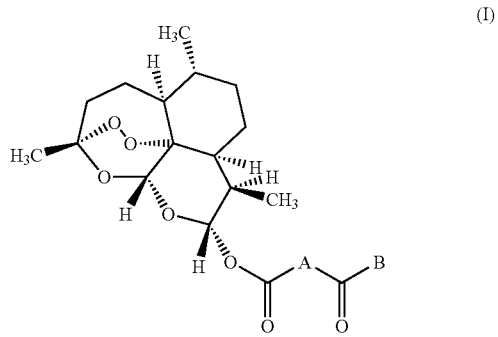

wherein A and B are as defined in the specification. Compounds (I) have proved able to inhibit cell proliferation, in particular of uveal melanoma cells, and can therefore be used, either alone or in association with other antitumoral drugs, for the preparation of medicaments intended for the treatment of malignant melanoma.

8 Claims, No Drawings

ARTEMISININ DERIVATIVES FOR THE TREATMENT OF MELANOMA

FIELD OF INVENTION

The present invention relates to Artemisinin derivatives useful for the treatment of malignant melanoma. In particular, the invention relates to esters of Artemisinin with dicarboxylic acids.

BACKGROUND OF THE INVENTION

Artemisinin, of formula

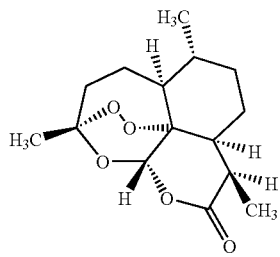

is an active ingredient of plant origin which was isolated in 1972 from the leaves of *Artemisia annua* L., a shrub which had long been used in Chinese traditional medicine to treat fever and malaria. Due to its ability to interfere with the regulation of the genes involved in the control of cell proliferation, angiogenesis and apoptosis, Artemisinin has also proved active in the treatment of uveal cancer at nanomolar concentrations, with toxicity comparable to that of conventional antitumoral drugs. A semisynthetic derivative of Artemisinin, Artesunate,

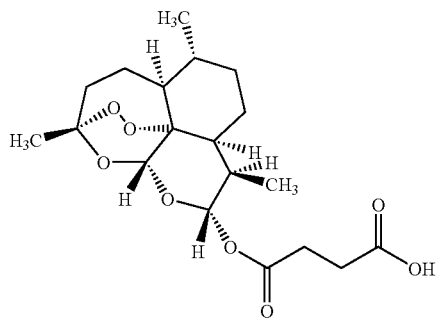

obtained by reduction of the ketone group at the 12-position of Artemisinin and subsequent esterification with succinic acid, is used either alone or in association with other malaria drugs, but has also proved effective in the treatment of metastatic uveal melanoma in association with standard chemotherapy.

Some Artemisinin derivatives are also known, such as 12-dihydroartemisinin, dihydroartemisinin 12-benzoate, 12-(2'-hydroxyethyl)deoxyartemisinin, the 12(2'-ethylthio) dimer of deoxyartemisinin and the trimer of deoxyartemisinin. This latter compound, in particular, has a powerful antitumoral effect ($CI_{50}$=6.0 μM), even greater than that of paclitaxel ($CI_{50}$=13.1 μM), on the cell line of oral cancer (YD-10B); it also induces apoptosis through a caspase-3-dependent mechanism.

It would be therefore advantageous to have further Artemisinin derivatives which possess improved antitumoral activity.

DESCRIPTION OF THE INVENTION

The present invention relates to derivatives of Artemisinin, in particular of 12-dihydroartemisinin, with dicarboxylic acids. In particular the invention relates to compounds of general formula (I)

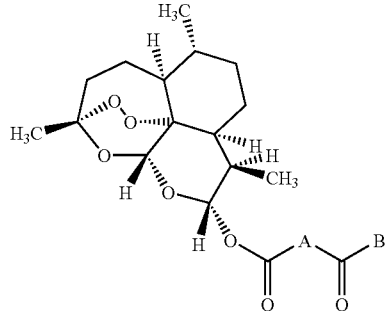

wherein

A represents a —($CH_2$)$_n$— group wherein n is an integer between 1 and 6, or a 5- or 6-membered carbocyclic ring, optionally containing one or more heteroatoms selected from N, O and S, and B represents an OH group or a group of formula:

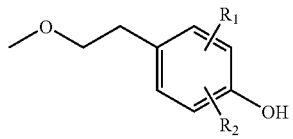

wherein $R_1$ and $R_2$ independently represent hydrogen, hydroxy, $C_1$-$C_5$ straight-chain or branched alkoxy or an aryloxy group, preferably phenoxy, with the exclusion of the compound of formula:

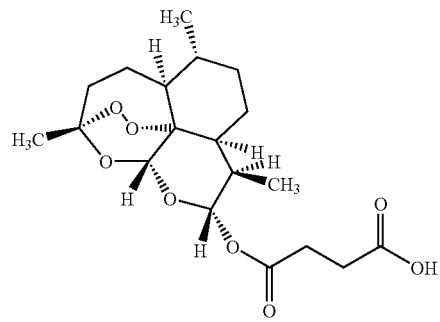

A first group of preferred compounds is the one wherein:

A represents a 5- or 6-membered carbocyclic ring, optionally containing one or more heteroatoms selected from N, O and S, and B represents an OH group.

A second group of preferred compounds is the one wherein:

A represents a —($CH_2$)$_n$— group wherein n is an integer between 1 and 6, and B represents a group of formula:

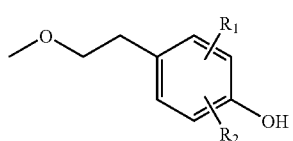

wherein $R_1$ and $R_2$ are as defined above.

The compounds according to the invention can be prepared in yields of up to 95% from 12-dihydroartemisinin by esterification with a suitable dicarboxylic acid, optionally followed by esterification with an alcohol of formula:

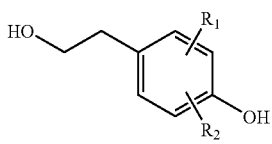

wherein $R_1$ and $R_2$ are as defined above.

Esterification reactions can be effected under biocatalytic conditions, for example with lipase, esterase from *Bacillus stearothermophilus*, horse liver, *Saccharomyces cerevisiae*, or in conditions of homogenous or heterogeneous catalysis of dicarboxylic aliphatic, aromatic or heterocyclic acids according to methods well-known to the skilled chemist.

Specific examples of the compounds according to the invention are as follows:

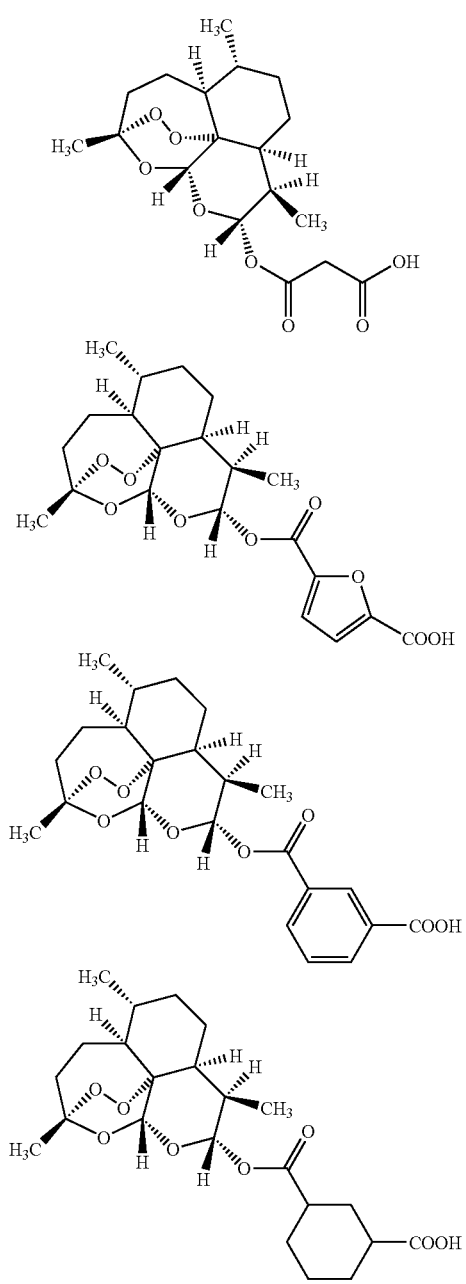

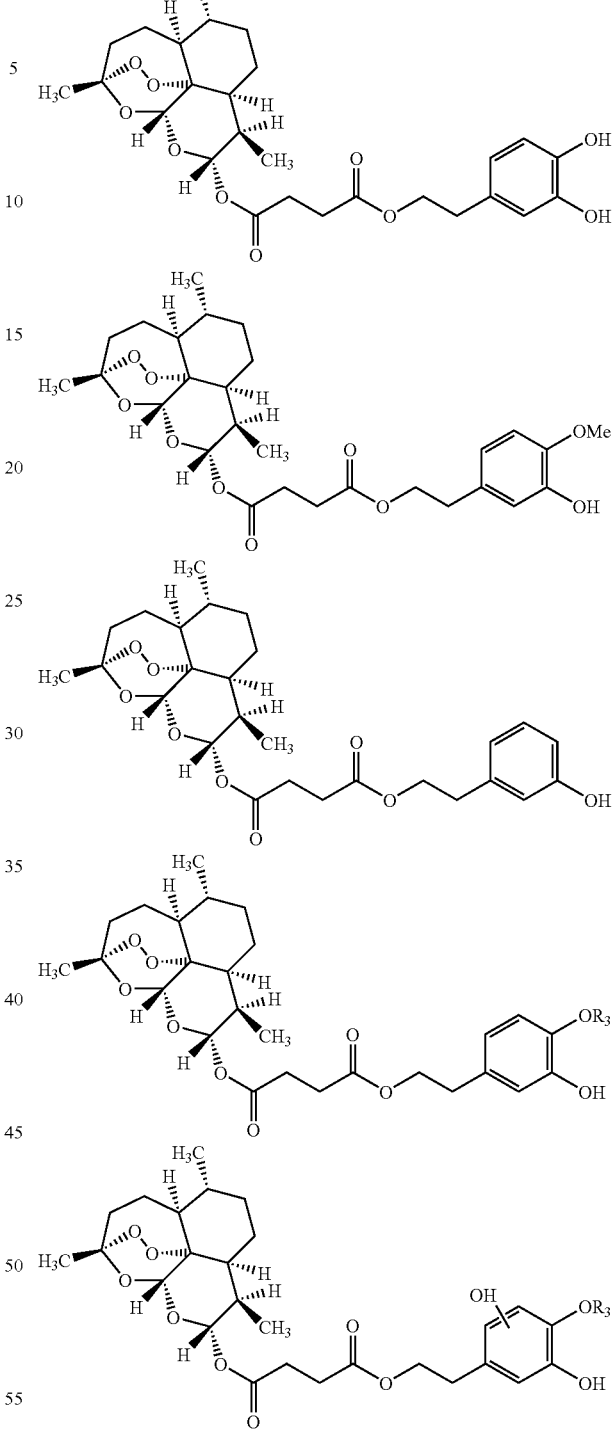

wherein $R_3$ independently represents hydrogen, a straight-chain or branched alkyl group or an aryl group optionally containing one or more heteroatoms selected from N, O and S, usually a methyl.

Procedure for the Prepare Ester Derivatives of Dihydroartemisinin, Including Artesunate The ester derivatives of dihydroartemisinin (DHA) were prepared with the chemical and biocatalytic procedures reported in the literature. By way of example, two selected procedures are shown below, a chemical and a biocatalytic procedure, for the general preparation procedure of DHA esters with fatty acids.

Procedure A: Biocatalytic Esterification of DHA with Lipase.

1 mmole of DHA is placed in acetone (5 mL) and treated with a catalytic amount of Lipase (e.g. Lipase from *Candida antartica*) whose activity was recently determined, operating at the temperature of 30° C. for 24 hours, in the presence of gentle (magnetic or orbital) stirring. The progress of the reaction is monitored by thin-layer chromatography (TLC, Merck or similar) using a chloroform:methanol 9.0:1.0 to 8.0:2.0 mixture as the eluent. When necessary, the progress of the reaction was monitored with high performance liquid chromatography (HPLC) in direct phase (for example: Nucleosil-NH2 column, acetonitrile:water 94:6.0 eluent) or, when necessary, in reversed phase with standard procedures. At the end of the reaction the solvent is evaporated off under conditions of reduced pressure, and the product is isolated from the reaction mixture by crystallisation or purification (flash-chromatography), depending on the nature of the fatty acid used for the reaction. The structure of the reaction products is confirmed with nuclear magnetic resonance (NMR) spectroscopy analysis. Ester yields ranging between 40 and 98% are obtained.

Procedure B: Chemical Esterification of DHA with the Anhydride Method.

1 mmole of DHA is placed in ethyl acetate (5 mL; or in the absence of organic solvent if the anhydride is liquid) and treated with an excess of fatty acid anhydride (3.0 equivalents) in the presence of a catalytic amount of sulphuric acid (5 drops). The reaction is conducted at a variable temperature (25° C. to 100° C.) and for variable times (10 min to 24 hours), depending on the nature of the anhydride. The progress of the reaction is monitored with thin-layer chromatography (TLC, Merck or similar) using a mixture of chloroform:methanol from 9.0:1.0 to 8.0:2.0 as eluent. When necessary, the progress of the reaction was monitored with high performance liquid chromatography (HPLC) in direct phase (for example: Nucleosil-NH2 column, acetonitrile:water 94:6.0 eluent) or, when necessary, in reverse phase with standard procedures. At the end of the reaction the solvent is evaporated off under reduced pressure conditions, and the product is isolated from the reaction mixture by crystallisation or purification (flash chromatography), depending on the nature of the fatty acid used for the reaction. The structure of the reaction products is confirmed with nuclear magnetic spectroscopy (NMR) analysis. Ester yields ranging between 40 and 98% are obtained.

The propionate and butyrate esters of DHA were obtained by the procedures indicated above. Their characterisation with Nuclear Magnetic Resonance spectroscopy is set out below:

Propionate ester of DHA—$^1$H-NMR (CDCl$_3$, 200 MHz) δ ppm: 6.28 (1H, m, CH(O)$_2$); 5.16 (1H, m, CH(O)$_2$); 5.11 (1H, m, CH(O)$_2$); 2.39-2.33 (2H, m, CH$_2$CO); 2.18 (1H, m, CH); 2.06-1.80 (2H, m, CH$_2$); 1.68-1.06 (2H, m, CH$_2$); 1.63 (1H, m, CH); 1.61 (1H, m, CH); 1.63-1.33 (2H, m, CH$_2$); 1.57 (2H, m, CH$_2$); 1.33 (1H, m, CH); 1.19 (2H, m, CH$_2$); 1.13-1.14 (3H, t, CH$_3$); 0.96 (3H, m, CH$_3$); 0.94 (3H, m, CH$_3$).

$^{13}$C-NMR (CDCl$_3$, 200 MHz) δ ppm: 175.27 (COO); 98.34 (OCHO); 93.62 (OCHO); 92.82 (OCHO); 81.36 (C); 43.06 (CH); 35.53 (CH); 34.79 (CH); 33.99 (CH$_2$); 33.47 (CH); 28.64 (CH$_2$); 27.95 (CH$_2$); 26.9 (CH$_2$); 26.77 (CH$_2$); 24.11 (CH$_2$); 19.76 (CH$_3$); 17.82 (CH$_3$); 9.13 (CH$_3$).

Butyrate ester of DHA —$^1$H-NMR (CDCl$_3$, 200 MHz) δ ppm: 6.23 (1H, m, CH(O)$_2$); 5.16 (1H, m, CH(O)$_2$); 5.11 (1H, m, CH(O)$_2$); 2.36-2.33 (2H, m, CH$_2$CO); 2.18 (1H, m, CH); 2.06-1.80 (2H, m, CH$_2$); 1.68-1.06 (2H, m, CH$_2$); 1.63 (1H, m, CH); 1.61 (1H, m, CH); 1.62 (2H, m, CH$_2$); 1.63-1.33 (2H, m, CH$_2$); 1.57 (2H, m, CH$_2$); 1.33 (1H, m, CH); 1.19 (2H, m, CH$_2$); 0.98 (3H, m, CH$_3$); 0.96 (3H, m, CH$_3$); 0.94 (3H, m, CH$_3$). $^{13}$C-NMR (CDCl$_3$, 200 MHz) δ ppm: 172.30 (COO); 98.34 (OCHO); 93.62 (OCHO); 92.87 (OCHO); 81.36 (C); 43.06 (CH); 36.3 (CH$_2$); 35.53 (CH); 34.79 (CH); 33.99 (CH$_2$); 33.47 (CH); 26.9 (CH$_2$); 26.77 (CH$_2$); 24.11 (CH$_2$); 26.77 (CH$_2$); 24.11 (CH$_2$); 19.76 (CH$_3$); 18.3 (CH$_2$); 17.82 (CH$_3$); 13.5 (CH$_3$).

The compounds of the invention have proved able to vary the potential internal cell redox and interfere with the melanogenic pathway. They can therefore be used, either alone or in association with other antitumoral drugs, for the preparation of medicaments intended for the treatment of tumours, in particular malignant melanoma. The compounds of the invention can be formulated for oral or intravenous administration with conventional techniques and excipients, such as those described in Remington's Pharmaceutical Science HandBook, 21st edition.

Specific examples of formulations are set out below.

EXAMPLE 1

268 mg Tablets Containing 50 mg of Active Ingredient

| Ingredient | (%) |
|---|---|
| Compound of formula (I) | 18.7 |
| Microcrystalline cellulose | 44.8 |
| Pre-gelatinised corn starch | 13.0 |
| Carboxymethyl starch | 0.7 |
| Calcium phosphate dibasic dihydrate | 16.8 |
| Magnesium stearate | 1.5 |
| Amorphous silica | 1.5 |
| Talc | 3.0 |

EXAMPLE 2

100 g Drinkable Solution Containing 0.75% of Active Ingredient

| Ingredient | (%) |
|---|---|
| Compound of formula (I) | 0.75 |
| Ethanol | 3.00 |
| Liquid sorbitol | 21.0 |
| Methyl para-hydroxybenzoate | 0.15 |
| Butyl para-hydroxybenzoate | 0.015 |
| Cherry flavouring | 0.075 |
| Saccharine | 0.075 |
| Water | 75.0 |

EXAMPLE 3

1 g Soluble Granulate Sachets, Containing 50 mg of Active Ingredient

| Ingredient | (%) |
|---|---|
| Compound of formula (I) | 5.0 |
| PVP | 0.4 |
| Carboxymethyl starch | 0.7 |
| Sodium saccharine | 1.0 |
| Orange granulate | 4.0 |
| Lemon granulate | 4.0 |
| Saccharose | 84.9 |

EXAMPLE 4

400 mg Capsules Containing 50 mg of Active Ingredient

| Ingredient | (%) |
|---|---|
| Compound of formula (I) | 12.4 |
| Microcrystalline cellulose | 44.8 |
| Lactose | 29.9 |
| Calcium phosphate dibasic dihydrate | 6.2 |
| Magnesium stearate | 1.5 |
| Amorphous silica | 3.7 |
| Talc | 1.5 |

The invention claimed is:

1. A compound of general formula (I)

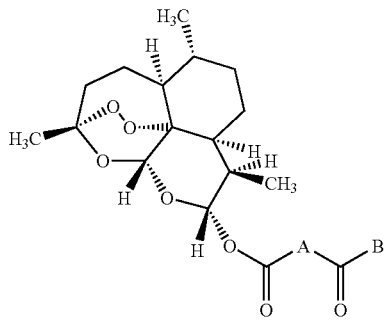

(I)

wherein,

A represents a —$(CH_2)_n$— group wherein n is an integer between 1 and 6, and

B represents a group of formula

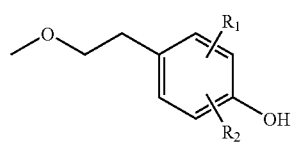

wherein $R_1$ and $R_2$ independently represent hydrogen, hydroxy, $C_1$-$C_5$ alkoxy, straight-chain or branched, an aryloxy group, or phenoxy, excluding the compound of formula:

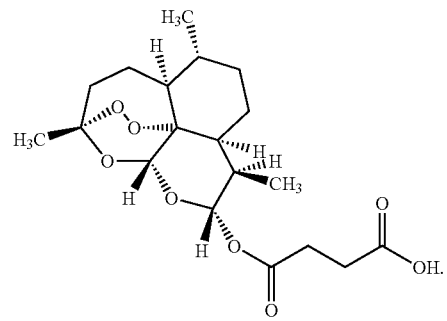

2. A compound of formula (I)

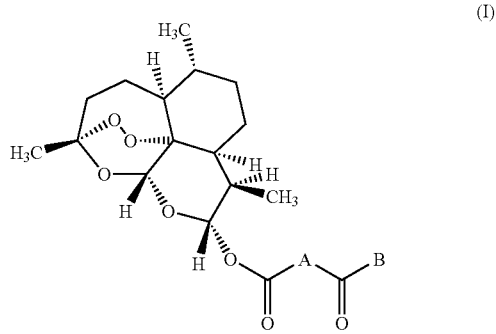

(I)

wherein:

A represents a 5- or 6- member carbocyclic ring, optionally containing one or more heteroatoms selected from N, O and S, and B represents an OH group.

3. The compound according to claim 1, selected from:

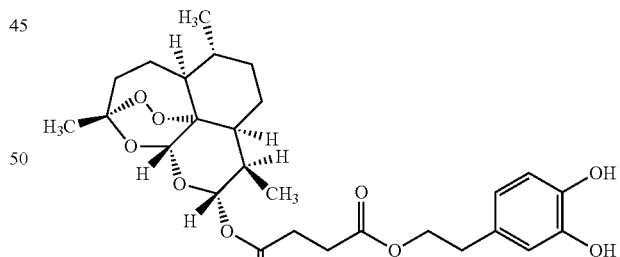

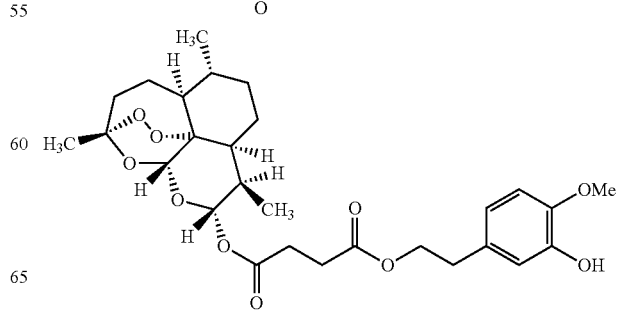

-continued

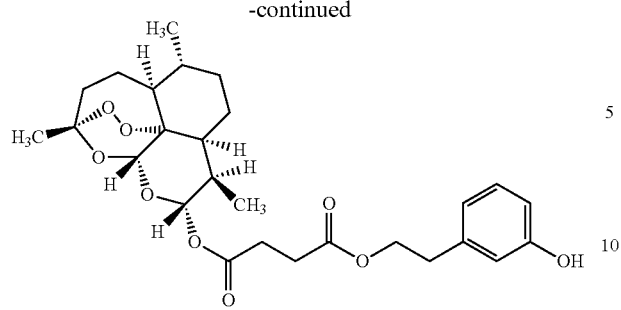

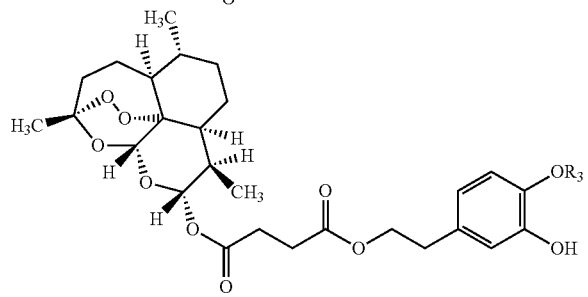

and

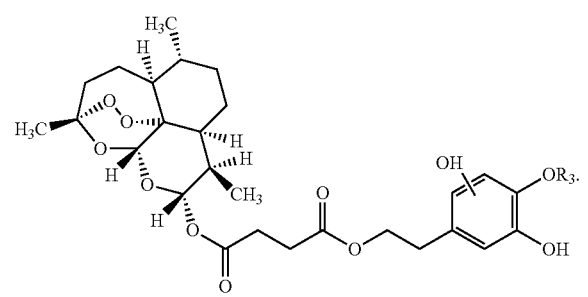

4. A pharmaceutical composition comprising a compound according to claim 1 in combination with suitable excipients and/or vehicles.

5. The pharmaceutical composition according to claim 4, further comprising one or more known antitumoral drugs.

6. The compound according to claim 2, selected from:

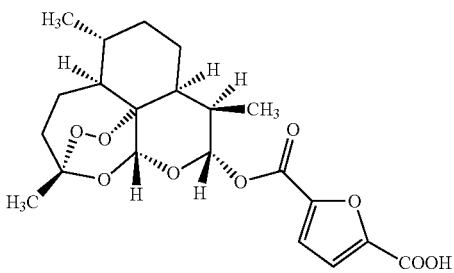

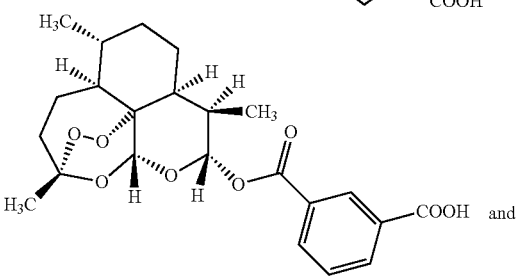

and

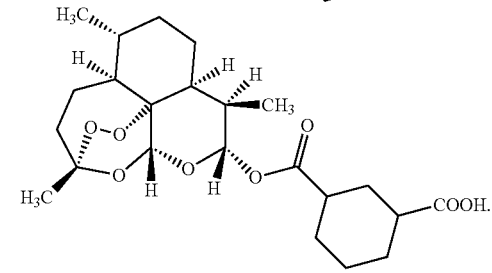

7. A pharmaceutical composition comprising a compound according to claim 2 in combination with suitable excipients and/or vehicles.

8. The pharmaceutical composition according to claim 7, further comprising one or more known antitumoral drugs.

* * * * *

UNITED STATES PATENT AND TRADEMARK OFFICE
CERTIFICATE OF CORRECTION

PATENT NO. : 8,507,698 B2  Page 1 of 1
APPLICATION NO. : 12/679916
DATED : August 13, 2013
INVENTOR(S) : Villanova et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 523 days.

Signed and Sealed this

Fifteenth Day of September, 2015

Michelle K. Lee
*Director of the United States Patent and Trademark Office*